(12) United States Patent
Petersen et al.

(10) Patent No.: US 7,701,193 B2
(45) Date of Patent: Apr. 20, 2010

(54) PULSE HEIGHT ANALYSER

(75) Inventors: Freddy Petersen, Jyllinge (DK); Rune Funder Mikkelsen, Herlev (DK); Morten Wilsbech, Hillerød (DK)

(73) Assignee: Chempaq A/S, Farum (DK)

( * ) Notice: Subject to any disclaimer, the term of this patent is extended or adjusted under 35 U.S.C. 154(b) by 437 days.

(21) Appl. No.: 10/570,150

(22) PCT Filed: Aug. 27, 2004

(86) PCT No.: PCT/DK2004/000568

§ 371 (c)(1),
(2), (4) Date: Oct. 30, 2006

(87) PCT Pub. No.: WO2005/022126

PCT Pub. Date: Mar. 10, 2005

(65) Prior Publication Data

US 2007/0200548 A1    Aug. 30, 2007

(30) Foreign Application Priority Data

Sep. 2, 2003  (DK) ............................... 2003 01257

(51) Int. Cl.
  *G06M 1/00* (2006.01)
  *G01D 1/14* (2006.01)
(52) U.S. Cl. ................... 324/76.16; 324/76.13
(58) Field of Classification Search .............. 324/76.16, 324/76.13, 76.12, 76.11
  See application file for complete search history.

(56) References Cited

U.S. PATENT DOCUMENTS

| 3,345,502 | A | | 10/1967 | Berg et al. | |
|---|---|---|---|---|---|
| 3,502,993 | A | | 3/1970 | Schurzinger et al. | |
| 3,634,688 | A | * | 1/1972 | Di Rocco | 250/366 |
| 3,790,767 | A | * | 2/1974 | Alexander | 702/108 |
| 3,801,904 | A | | 4/1974 | Hogg et al. | |
| 4,093,866 | A | * | 6/1978 | Kasdan et al. | 250/559.39 |
| 4,218,610 | A | | 8/1980 | Baxter, Jr. et al. | |
| 4,365,193 | A | * | 12/1982 | Bollero et al. | 324/102 |
| 4,541,070 | A | * | 9/1985 | Musin et al. | 702/73 |
| 4,817,208 | A | * | 3/1989 | Koch et al. | 398/202 |
| 4,879,464 | A | * | 11/1989 | Iinuma | 250/361 R |

(Continued)

FOREIGN PATENT DOCUMENTS

GB    1 457 657    12/1976

OTHER PUBLICATIONS

Kachel, Volker, Electrical Resistance Pulse Sizing: Coulter Sizing, 1990, pp. 45-80, Flow Cytometry and Sorting, Second Edition.

*Primary Examiner*—Hoai-An D Nguyen
(74) *Attorney, Agent, or Firm*—Volentine & Whitt, P.L.L.C.

(57) ABSTRACT

A pulse height analyzer for determination of the pulse height distribution of electronic pulses includes a set of comparators with a common input for analogue to digital conversion of the electronic pulses, a set of latches wherein the inputs of the latches are connected to the outputs of respective comparators for recording passage of the corresponding threshold voltages by the rising edge of a pulse, a priority encoder connected to the latch outputs for determination of a pulse height category consisting of pulses with a pulse height within a pulse height interval defined by respective threshold voltages, and a micro controller that is adapted to count the number of pulses within each pulse height category.

9 Claims, 3 Drawing Sheets

U.S. PATENT DOCUMENTS 5,357,331 A * 10/1994 Flockencier ............... 356/5.08
5,528,303 A *  6/1996 Bee et al. .................... 348/531
5,719,667 A *  2/1998 Miers .......................... 356/73
2003/0105397 A1* 6/2003 Tumer et al. ................ 600/436

* cited by examiner

PULSE HEIGHT ANALYSER

CROSS REFERENCE TO RELATED APPLICATIONS

This application is the national phase under 35 U.S.C. 371 of PCT International Application No. PCT/DK2004/000568 which has an international filing date of Aug. 27, 2004, and also claims priority under 35 U.S.C. 119 to Danish application PA 2003 01257 filed on Sep. 2, 2003, both of which applications are hereby incorporated by reference in their entirety for all purposes as if fully set forth herein.

BACKGROUND OF THE INVENTION

1. Field of the Invention

The present invention relates to a particle characterisation apparatus in which particles suspended in a liquid are passed through an orifice, in principle one by one, to enable the characterisation of the particles, for instance by Coulter counting.

2. Description of the Related Art

It is well-known that particles travelling through a small orifice can be characterised with respect to size, concentration and conductivity by the use of an electrical impedance technique, widely known as the Coulter sizing (see V. Kachel, "Electrical Resistance Pulse Sizing: Coulter Sizing", Flow Cytometry and Sorting, Second Edition, pp. 45-80, 1990 Wiley-Liss).

Counting and sizing of particles by the Coulter principle is an internationally respected method that is being used in most haematology-analysers and particle counting equipment. The method is based on measurable changes in the electrical impedance produced by non-conductive particles in an electrolyte. A small opening, called the "aperture" or "orifice", connects two electrically isolated chambers, where electrodes have been provided to contact the electrolyte. The orifice applies a restriction to the electrical path, whereby a sensing zone is established through which the particles are aspirated. In the sensing zone each particle will give rise to a displacement of the surrounding electrolyte, thus blocking part of the current-path and giving rise to a voltage pulse. By this method several thousand particles per second can be characterised with high precision.

It is also well-known that the peak amplitude of the voltage pulses generated by the particles are closely correlated to the size of the particles, and therefore it is desirable to be able to determine the peak amplitude of voltage pulses in a simple and reliable way and at a low cost.

BRIEF SUMMARY OF THE INVENTION

According to the present invention these and other objects are fulfilled by a pulse height analyser for determination of the pulse height distribution of electronic pulses wherein the pulse height of each pulse is determined by recording of the passage of a set of voltage thresholds by the positive going edge of the pulse. The maximum threshold exceeded by the pulse characterises the peak amplitude of the pulse. Identification of the maximum exceeded threshold is input to a micro controller that is adapted to count the number of pulses within a pulse height category. A pulse height category consists of pulses with a pulse height within a pulse height interval defined between respective threshold voltages.

Thus, the pulse height analyser may comprise a set of comparators with a common input that is provided with the electronic pulses.

Further, the pulse height analyser may comprise a set of latches wherein the inputs of the latches are connected to the outputs of respective comparators for recording passage of the corresponding threshold voltages by the rising edge of a pulse.

Identification of the set latched comparator outputs is input to the micro controller.

A priority encoder may be connected to the latch outputs for determination of a pulse height category consisting of pulses with a specific maximum exceeded threshold voltage. This minimises the number of inputs to the micro controller for provision of the category identification.

Further, the pulse height analyser may comprise a filter for provision of a substantially constant delay from pulse start to maximum pulse amplitude of the filtered pulse so that the time from pulse start to recording of the peak pulse amplitude is fixed whereby the electronic circuitry and especially the micro controller software handling the recorded measurement and controlling termination of the recording is simplified.

The filter may be designed so that the output signal from the filter substantially has no DC-component. For example, the filter may differentiate the electronic pulses. Then, the filter output signal will contain a positive peak caused by the leading edge of an input pulse, and a negative peak caused by the trailing edge of the input pulse. The DC-components of the positive and negative peaks substantially cancel each other so that the resulting DC-component of the filter output signal substantially equals zero. This eliminates a need for a restoration circuit to compensate for possible DC baseline variations in the filter output signal due to variations in the mean value of the input signal containing the electronic pulses.

It is an important advantage of the present invention that the threshold voltages may be individually adjusted as desired. For example, it is not required that the threshold voltages are equidistant. If the possible sizes of the particles are known, it is possible to select a minimum number of threshold voltages that are adjusted for optimum determination of the size distribution of the particles.

For example, in analysis of whole blood, it is desirable to count the number of three types of blood cells erythrocytes, leukocytes and thrombocytes. Their size, expressed as equivalent diameter or volume, ranges from app. 1.2 µm or 1 fl (1 fl=$10^{-15}$ l) for the smallest thrombocytes to app. 9 µm or 400 fl for the largest leukocytes.

Information on the content of leukocytes, their subpopulations and thrombocytes is an important tool for the physician in order to diagnose different diseases and monitor treatment. Furthermore, the concentration of haemoglobin, directly related to the number of erythrocytes, in the blood sample is also of great importance.

Thus, the number of erythrocytes, leukocytes and thrombocytes may be counted utilising the pulse height analyser of the present invention with threshold voltages that are selected and adjusted in accordance with the known sizes of the erythrocytes, leukocytes and thrombocytes, e.g. by positioning threshold voltages in between corresponding mean values of the individual particle size distributions.

Preferably, the pulse height analyser also contains a current source, preferably a constant current source, for connection to the electrodes contacting the electrolyte in the two chambers mutually connected by the orifice. A particle passing through the orifice generates the electronic voltage pulse across the electrodes, which is supplied to the pulse height analyser. The peak value of the pulse is proportional to the volume of the particle and the value of the current.

In a preferred embodiment of the invention, the threshold voltages of the comparators are made dependent on the actual value of the generated electrode current so that possible variations of the electrode current are substantially cancelled by corresponding variations of the thresholds. For example, the electrode current may be mirrored and the mirrored current supplied to a resistive voltage divider providing the threshold voltages. Then, e.g., a decrease in the generated electrode current is compensated by a corresponding decrease of the threshold voltages.

The equivalent diameter of blood cells varies by a factor of app. 10 and thus, the volume of blood cells varies by a factor of app. 1000 so that the electronic pulses generated by the Coulter principle have a significant dynamic range. In order to lower the corresponding voltage range of the threshold voltages of the comparators, the comparators may be grouped in two or more sets of comparators, each set of comparators having a common signal input. Each signal input may be connected to an amplifier for amplification of the electronic pulses with an individual gain. Thus, considering the set of comparators connected to the amplifier with the largest gain, if the maximum amplified input pulse does not exceed the maximum threshold voltage of these comparators, the outputs of the comparators are used for determination of pulse height distribution. However, if the maximum threshold voltage is exceeded, then the next set of comparators connected to the next largest gain is used for determination of pulse height distribution, unless the maximum threshold voltage of these comparators is exceeded by the respective amplified input pulse, etc.

Having determined and recorded the pulse height, the latches are reset whereby the pulse height analyser is made ready for pulse height determination of the next pulse. A latch-reset pulse may be generated a predetermined and fixed time period after pulse start.

BRIEF DESCRIPTION OF THE DRAWINGS

In the following the invention will be further described and illustrated with reference to the accompanying drawings in which.

DETAILED DESCRIPTION OF PREFERRED EMBODIMENTS

Figure 1:
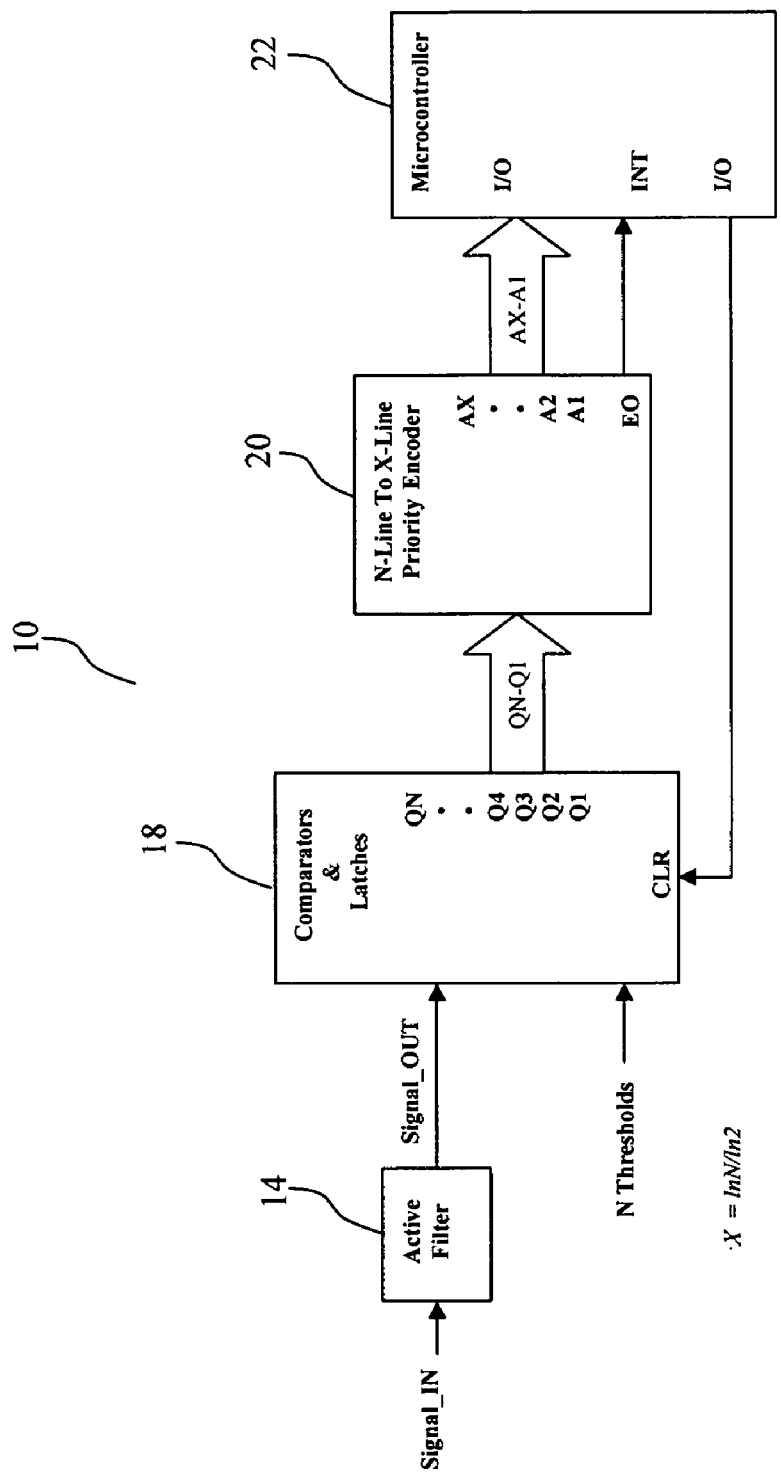
FIG. 1 is a blocked diagram of a preferred embodiment of the present invention.

FIG. 1 is a blocked diagram of a pulse height analyser 10 according to the present invention. The amplitude and frequency count of voltage pulses on the Signal_IN line is determined with the illustrated pulse height analyser 10. The operating principle of the analyser is described in the following with reference to the timing diagram of FIG. 2.

Figure 2:
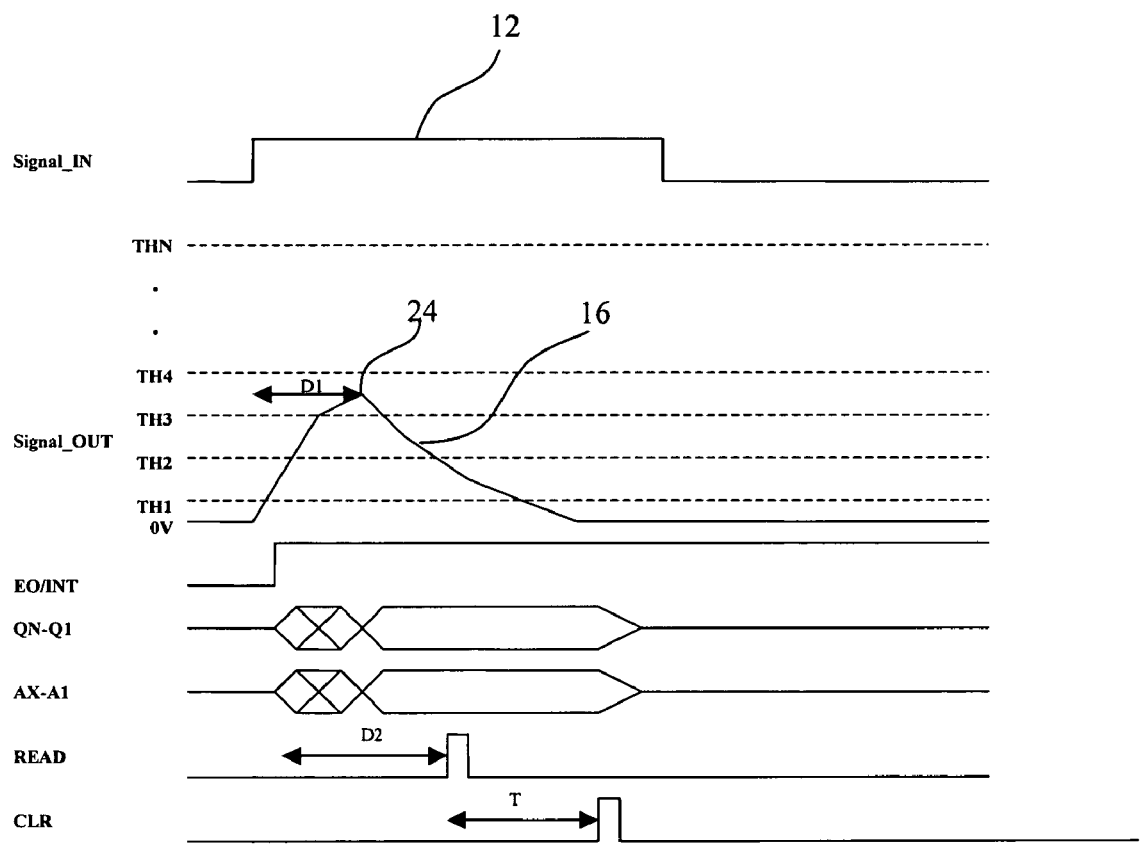
FIG. 2 is a timing diagram illustrating the operation of the embodiment shown in FIG. 1.

In FIG. 2, the voltage pulses 12 occurring on Signal_IN is illustrated as a square wave pulse. Typically, the pulses have varying pulse shapes with varying peak amplitudes, and varying pulse width.

The active filter 14 filters the input pulses 12, and the filtered output pulses 16 on the Signal_OUT line have a constant delay D1 between the peak amplitude 24 and the start of the rising edge of the pulses 16. D1 is independent of the peak amplitude of the pulses 12, 16. The ratio between the peak amplitude 24 of the filtered pulses 16 and the peak amplitude of respective input pulses 12 is substantially constant. As illustrated in FIG. 2, the pulse width of the output pulses is less than the pulse width of the input pulses. The determination of the pulse height 12 is independent of the pulse width of the input pulse 12.

The filtered output pulses 16 are provided to the N comparator & latches 18 with N thresholds. When the rising edge of the filtered pulse 16 passes a specific threshold THP (P=1, 2, . . . , N), e.g. threshold TH2 in FIG. 2, the corresponding latched output QP, e.g. Q2, is set. Thus, after D1 the latched outputs Q1, Q2, . . . , QN that correspond to the thresholds TH1, TH2, . . . , THN having been exceeded by the pulse in question are set. For example, in FIG. 2, the latched outputs Q1, Q2, and Q3 are set.

The N-Line to X-Line priority encoder 20 converts $Q_N$–$Q_1$ to a binary identifier $A_X$–$A_1$. In the example of FIG. 2, $Q_N$–$Q_1$=0 . . . 0111 is converted to binary $A_X$–$A_1$=0 . . . 0011. Thus the number of identifier bits is reduced. For example three identifier bits may identify up to 8 threshold voltages, four identifier bits may identify up to 16 threshold voltages, etc.

The Enable Output (EO) interrupts (INT) the micro controller 22 at the positive transition of EO generated when the rising edge of pulse 16 passes TH1. In a preferred embodiment, the latch output $Q_1$ is connected to INT instead of EO in order to eliminate interrupts on the trailing edge of pulse 16 in case pulse 16 is noisy.

The micro controller 22 contains a counter for each pulse height category so that the number of pulses occurring within each category may be counted. Preferably, consecutive threshold voltages define a pulse height category, i.e. output pulses 16 with peak amplitudes between thresholds TH1 and TH2 for which Q1 is set ($Q_N$ . . . $Q_2Q_1$=0 . . . 0001) constitutes one pulse height category, and output pulses 16 with peak amplitudes between thresholds TH2 and TH3 for which Q1 and Q2 is set ($Q_N$ . . . $Q_2Q_1$=0 . . . 0011) constitutes the next pulse height category, etc.

Upon interrupt, the micro controller 22 performs the following steps:

1) Wait D2>D1 so that $A_X$–$A_1$ is stable (cf. FIG. 2),
2) READ $A_X$ . . . $A_3A_2A_1$ (0 . . . 0011 in the example of FIG. 2),
3) Increment by one the counter in the micro controller 22 that counts the number of pulses 16 with the same peak amplitude recording, e.g. in the example of FIG. 2, the counter counting the number of pulses 16 with a peak amplitude 24 ranging from TH3 to TH4, and
4) Send CLR to the latches and the circuit is ready to receive the next pulse.

This procedure is repeated and executed in the measurement window. Measurement START and STOP signal to the micro controller 22 are not show in FIG. 1.

The priority encoder 20 may be realised with a 74HC148 8-Line to 3-Line priority encoder for N=8 and X=3.

Two 74HC148 8-Line to 3-Line Priority Encoder and three 2-input AND gates may be interconnected for provision of four binary identification bits, i.e. N=16 and X=4 as is well known in the art.

Likewise, as is also well-known in the art, 4 or 8 or 16 etc 74HC148 8-Line to 3-Line priority encoders and 3+4=7 or 7+5=12 or 12+6=18 etc 2-input AND gates may be interconnected for provision of five, six or seven, respectively, binary identification bits, i.e. N=32, 64, or 128, and X=5, 6, or 7, respectively.

In another embodiment of the present invention, the latches and priority encoder is embodied in a field programmable gate array (FPGA).

In yet another embodiment of the present invention, the circuitry illustrated in FIG. 1, exclusive the micro controller 22, is embodied in a hybrid application specific integrated circuit (ASIC) containing analogue and digital circuitry.

Figure 3:
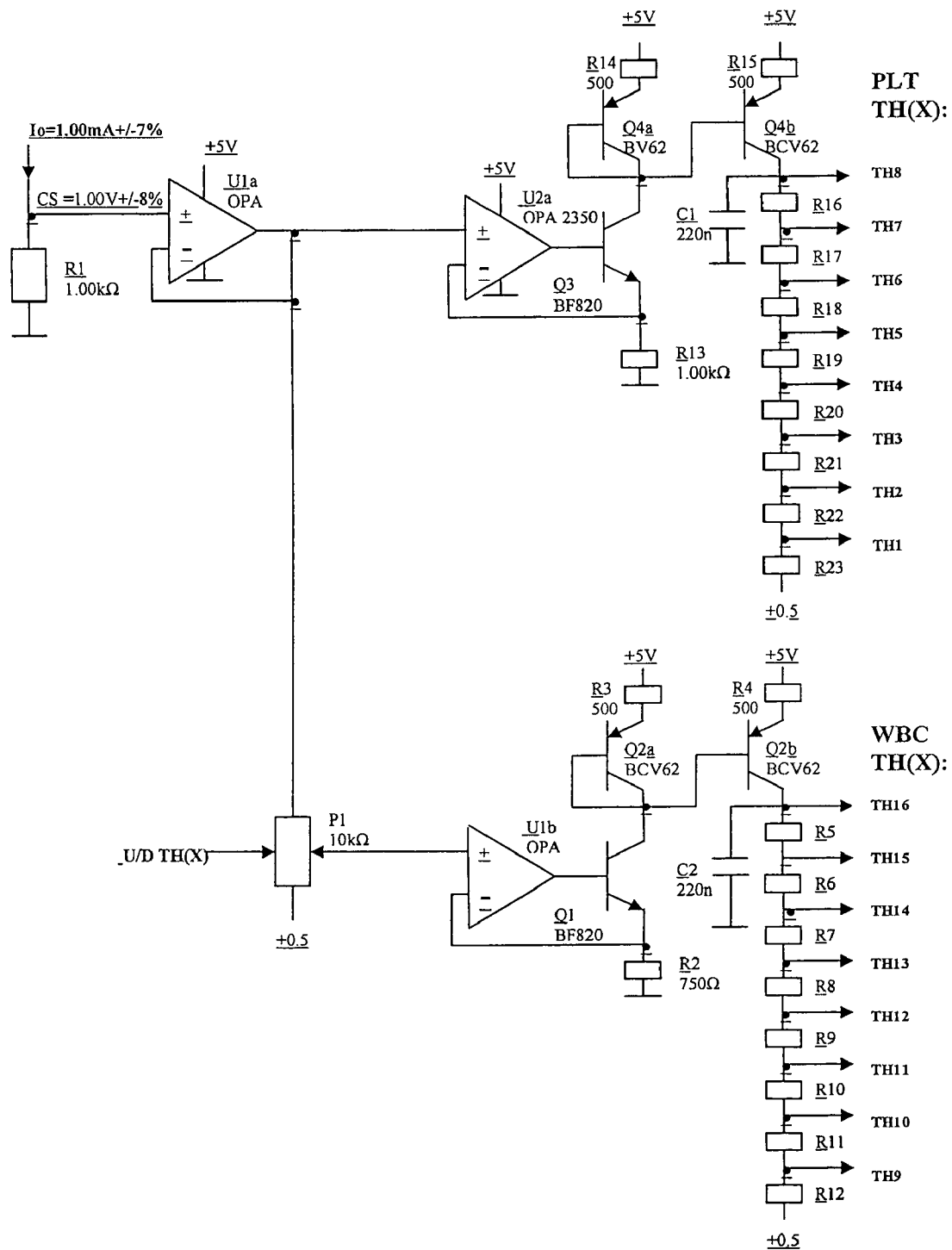
FIG. 3 shows a circuit diagram of an electronic circuit for generation of threshold voltages derived from the electrode current.

FIG. 3 illustrates a circuit of a preferred embodiment for generation of threshold voltages. $I_o$ is the generated constant electrode current of 1.00 mA±7%. $I_o$ generates a voltage $V_o$ across $R_1$. $U_{1a}$ is a voltage follower, and $U_{2a}$ generates the same voltage $V_o$ across $R_{13}$ so that $I_{TH1}$ is substantially equal to $I_o$. It should be noted that the threshold voltages $P_1$ to $P_8$ generated in the voltage divider $R_{16}$ to $R_{23}$ by $I_{TH1}$ vary proportionally til $V_o$ but apart from this variation, the threshold voltages $P_1$ to $P_8$ are fixed. These threshold voltages are used for counting platelets (PLT).

Further, the output voltage of the voltage follower is voltage divided by the programmable potentiometer $P_1$, and $U_{1b}$ generates the divided voltage $U_{P1}$ across $R_2$. The current generated through $R_2$ is mirrored into the voltage divider $R_5$ to $R_{12}$ generating the threshold voltages C, L, M, $G_1$ to $G_5$. These threshold voltages are used for categorization of white blood cells (WBC). It should be noted that these threshold voltages vary proportionally to $I_o$ and that they are also adjustable via the control line U/D TH(X) for digital up/down adjustment of the potentiometer $P_1$. The adjustment is performed during calibration as described below.

In a preferred embodiment of the present invention, the aperture resides in a polymer membrane and is precision machined. Preferably, the aperture is machined with a UV-laser to provide an aperture diameter of 36 μm with a tolerance of ±2%. The aperture to aperture diameter variation (±2%) generates a pulse height tolerance of the electronic pulses of ±4%, since the pulse height is proportional to the cross sectional area of the aperture, and therefore, it is preferred to calibrate the instrument before particle size determination.

The invention claimed is:

1. A pulse height analyzer for determination of pulse height distribution of electronic pulses, comprising:
   a set of comparators provided with a common input, for analog to digital conversion of the electronic pulses into converted pulses,
   a set of latches wherein inputs of the latches are connected to outputs of respective comparators for recording passage of corresponding threshold voltages by rising edges of the converted pulses,
   a priority encoder connected to outputs of the latches for determination of pulse height categories consisting of converted pulses with a pulse height within pulse height intervals defined by the corresponding threshold voltages,
   a micro controller that is adapted to count a number of pulses within each of the pulse height categories, and
   a current source for connection to electrodes contacting an electrolyte in two chambers mutually connected by an orifice for Coulter counting of particles, wherein the threshold voltages of the comparators are dependent on an actual value of generated electrode current, and whereby possible variations of the electrode current are substantially cancelled by corresponding variations of the voltage thresholds.

2. A pulse height analyzer according to claim 1, wherein the current source is a constant current source.

3. A pulse height analyzer according to claim 1, further comprising a filter for filtering the electronic pulses to provide filtered pulses having a substantially constant delay from pulse start to maximum pulse amplitude, and for providing the filtered pulses as the common input of the comparators.

4. A pulse height analyzer according to claim 1, further comprising a filter for filtering the electronic pulses to provide an output signal containing filtered pulses with a DC-value substantially equal to zero.

5. A pulse height analyzer according to claim 1, further comprising a plurality of sets of comparators for pulse height determination of input electronic pulses of different amplification.

6. A pulse height analyzer according to claim 1, further comprising circuitry for resetting the latches a predetermined time period after start of a converted pulse, the time period being independent of the pulse height and pulse width.

7. An integrated circuit comprising the pulse height analyzer according to claim 1.

8. A field programmable gate array comprising the pulse height analyzer according to claim 1.

9. An application specific integrated circuit comprising the pulse height analyzer according to claim 1.

* * * * *